(12) United States Patent
Osypka

(10) Patent No.: US 9,078,581 B2
(45) Date of Patent: Jul. 14, 2015

(54) EPICARDIAL MAPPING ELECTRODE

(71) Applicant: Peter Osypka, Grenzach-Wyhlen (DE)

(72) Inventor: Peter Osypka, Grenzach-Wyhlen (DE)

(*) Notice: Subject to any disclaimer, the term of this patent is extended or adjusted under 35 U.S.C. 154(b) by 124 days.

(21) Appl. No.: 13/928,874

(22) Filed: Jun. 27, 2013

(65) Prior Publication Data
US 2014/0005513 A1  Jan. 2, 2014

(30) Foreign Application Priority Data

Jun. 28, 2012 (EP) .................... 12004848

(51) Int. Cl.
A61B 5/042 (2006.01)
A61N 1/05 (2006.01)

(52) U.S. Cl.
CPC ............. A61B 5/042 (2013.01); A61B 5/0422 (2013.01); A61N 1/0595 (2013.01); A61N 1/059 (2013.01)

(58) Field of Classification Search
CPC .... A61B 5/042; A61B 5/0422; A61N 1/0587; A61N 1/059; A61N 1/0595
USPC ................... 600/374, 375; 607/129, 130, 132
See application file for complete search history.

(56) References Cited

U.S. PATENT DOCUMENTS

| 5,607,462 A | 3/1997 | Imran |
| 5,785,706 A * | 7/1998 | Bednarek ........................ 606/41 |
| 5,849,033 A | 12/1998 | Mehmanesh et al. |
| 7,856,260 B1 | 12/2010 | Ryu |
| 2002/0002329 A1 | 1/2002 | Avitall |

FOREIGN PATENT DOCUMENTS

EP  2241279 A1  10/2010

* cited by examiner

Primary Examiner — Lee S Cohen
(74) Attorney, Agent, or Firm — Locke Lord LLP; Scott D. Wofsy; Arpita G. Buesing

(57) ABSTRACT

An epicardial mapping electrode suitable for temporarily mapping and/or stimulating the left ventricle after a cardiac surgery. The epicardial mapping electrode comprising a flexible tube having a proximal and a distal end and a longitudinal structure therebetween. The tube has at least one lumen. A movable insulated electrode lead arranged inside the lumen, the lumen together with the electrode lead extends longitudinally through said longitudinal structure, the electrode lead has at its distal end an electrical pole. The flexible tube has along the electrode lead a number of openings facing the surface of the heart said openings providing contact between the myocardial tissue and the electrical pole.

9 Claims, 4 Drawing Sheets

EPICARDIAL MAPPING ELECTRODE

CROSS-REFERENCE TO RELATED APPLICATIONS

This application claims under 35 U.S.C. §119(a) priority to and benefit of European Patent Application No. EP12004848 filed Jun. 28, 2012, which is incorporated by reference herein in its entirety.

BACKGROUND OF THE INVENTION

1. Field of the Invention

The present invention relates to an epicardial mapping electrode, and more particularly to an epicardial mapping electrode being able to monitor the left ventricle after a cardiac surgery in order to find a suitable location for biventricular stimulation of a heart.

2. Description of Related Art

Pacemakers for biventricular stimulation are known and are employed in particular for cardiac resynchronization therapy (CRT) to re-coordinate the beating of the two ventricles by pacing both simultaneously and specifically improving the contraction of the left ventricle for patients with weak heart rate. The pacemaker is implanted and connected to right-ventricular electrodes for the stimulation of a right ventricle of the heart and to left-ventricular electrodes for the stimulation of a left ventricle of the heart. The success of cardiac resynchronization therapy depends amongst other factors on the correct position of the left ventricular electrode. As the left ventricular electrode cannot be implanted directly into the left ventricle the left ventricular electrode is introduced by way of the coronary sinus and positioned in a lateral side branch which branches from that coronary sinus. The fixation and the position of the left ventricular electrode in the different parts of the coronary sinus are essential for the success of the resynchronization therapy.

The aim of the present invention is therefore to provide a mapping electrode helping the physician to find the best section for placing the left ventricular electrode and helping him to know whether the selected position of the left ventricular electrode is suitable for delivering electrical stimuli and possibly also for measuring electric activity.

The aim of the present invention is to provide the requirements for optimized cardiac resynchronization therapy.

Such conventional methods and systems have generally been considered satisfactory for their intended purpose. However, there is still a need in the art for epicardial mapping electrode that allows for monitoring the left ventricle after a cardiac surgery in order to find a suitable location for biventricular stimulation of the heart. The present invention provides a solution for these problems.

SUMMARY OF THE INVENTION

An epicardial mapping electrode suitable for temporarily mapping and/or stimulating the left ventricle after a cardiac surgery is disclosed. The epicardial mapping electrode comprising a flexible tube having a proximal and a distal end and a longitudinal structure therebetween. The tube has at least one lumen. A movable insulated electrode lead arranged inside the lumen, the lumen together with the electrode lead extends longitudinally through said longitudinal structure, the electrode lead has at its distal end an electrical pole.

The flexible tube has along the electrode lead a number of openings facing the surface of the heart said openings providing contact between the myocardial tissue and the electrical pole. The flexible tube can be made of flexible material selected from group consisting of silicone, Dacron, polyurethane, polyester, silk and polyimide. The flexible tube can have two lumens for inserting two electrode-leads which are adjustable towards each other. The electrode lead is a partly insulated coil.

In another aspect of the invention a stylet is placed inside the coil electrode.

In another aspect of the invention a nitinol thread is inserted into the flexible tube to support the design.

In yet another aspect of the invention fixing elements are placed at the outside of the flexible tube.

The epicardial mapping electrode further comprises an indifferent counter-electrode. The indifferent counter-electrode is a coil of the electrode lead extending longitudinally through the flexible tube or a coil which is separately placed at the proximal end of the flexible tube. The indifferent electrode is placed in the thorax area of the patient.

In another aspect of the invention two indifferent electrodes are placed directly adjacent and parallel to the centrally placed flexible tube containing the insulated electrode lead with the electrical pole at its distal end.

These and other features of the systems and methods of the subject invention will become more readily apparent to those skilled in the art from the following detailed description of the preferred embodiments taken in conjunction with the drawings.

BRIEF DESCRIPTION OF THE DRAWINGS

So that those skilled in the art to which the subject invention appertains will readily understand how to make and use the devices and methods of the subject invention without undue experimentation, preferred embodiments thereof will be described in detail herein below with reference to certain figures, wherein:

FIG. 2A is a cross sectional view of the epicardial mapping electrode taken along line 2A of FIG. 2;

FIG. 3A is a cross-sectional view of the epicardial mapping electrode taken along line 3A of FIG. 3.

DETAILED DESCRIPTION OF THE PREFERRED EMBODIMENTS

Figure 1:
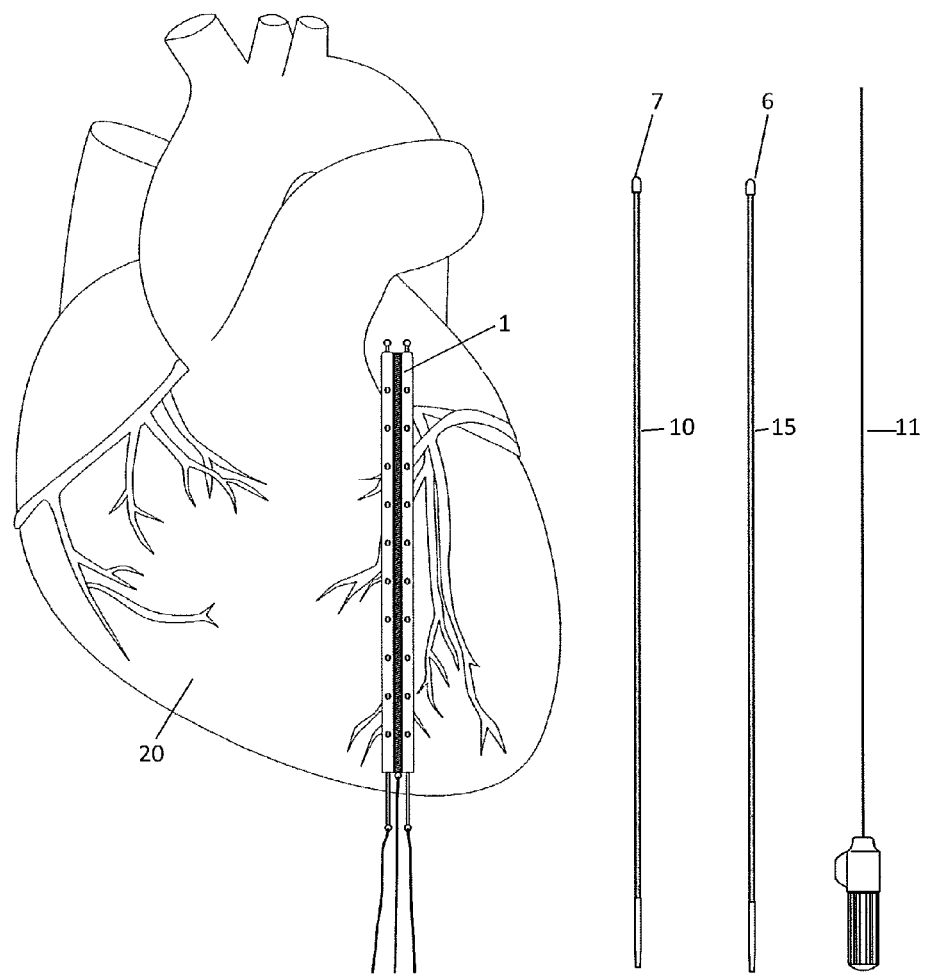
FIG. 1 is a perspective view showing the epicardial mapping electrode of the present invention contacting myocardial tissue.

Reference will now be made to the drawings wherein like reference numerals identify similar structural features or aspects of the subject invention. For purposes of explanation and illustration, and not limitation, a partial view of an exemplary embodiment of the epicardial mapping electrode in accordance with the invention is shown in FIG. 1 and is designated generally by reference character 1. Other embodiments of the epicardial mapping electrode in accordance with the invention, or aspects thereof, are provided in FIGS. 3 and 4, as will be described.

FIG. 1 shows the epicardial mapping electrode 1 contacting myocardial tissue 20. The flexible tube comprises two electrode leads 10 and 15 having on their distal end electrical poles 6 and 7. The electrode leads 10 and 15 are insulated coils. Stylet 11 placed inside the coil electrodes serves to stiffen the mapping electrode during handling thus achieving better control when moving the electrode leads. After the cardiac surgery the surgeon decides with closed heart and open thorax where to place the electrode device on the myocardial tissue.

Figure 2:
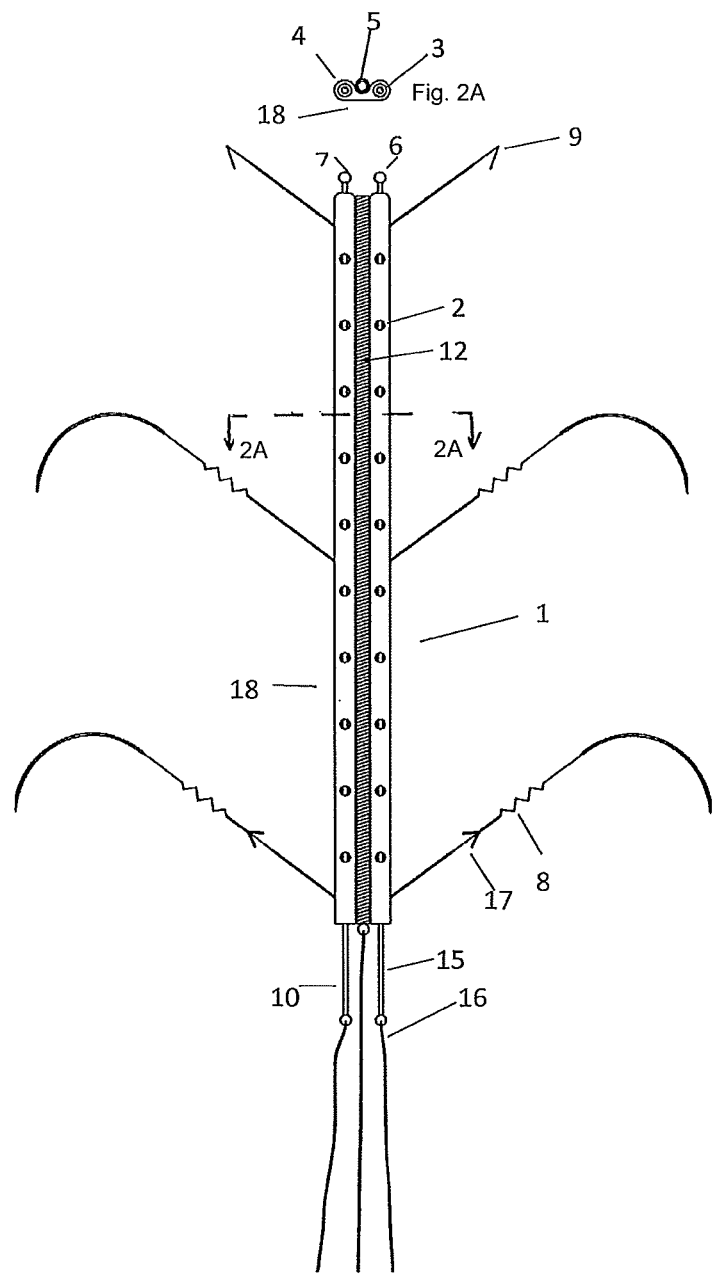
FIG. 2 is a front view showing the epicardial mapping electrode of FIG. 1 in more detail.

FIG. 2 shows the epicardial mapping electrode 1 of FIG. 1 in more detail. The mapping electrode consist of a flexible elongated tube 18 having a proximal and a distal end, and having two lumen 3 and 4 extending from the proximal to the distal end for inserting insulated electrode leads 10 and 15 with their associated electrical poles 6 and 7.

The flexible tube has along each inserted electrode lead a number of openings 2 facing the surface of the heart said openings providing contact between the myocardial tissue and the electrode pole. The openings 2 are aligned in a vertical line which is coaxial to the longitudinal axis of the tube 18.

The electrode leads 10 and 15 with their associated electrical poles 6 and 7 can move freely inside the lumen and are adjustable towards each other. Thus, the poles 6 and 7 can move from one opening to the other. When reaching an opening the electrical potential of the surface area of the heart associated to said opening is measured. By moving the poles the surface of the heart is scanned allowing mapping of the electrical activity of the heart.

The electrode leads 10 and 15 are flexible and consist of an insulated shaft preferably partly insulated coils.

In the center of the flexible tube 18 a depression 5 extends from the proximal to the distal end used to hold the indifferent electrode, preferably a coil shaped indifferent electrode 12. A conducting line 16 is attached to the electrode lead for measuring the signals provided by the cardiac activity. The conducting line is led to the outside through an opening in the patient thorax.

Fixing elements for fixing the mapping electrode at the myocardial tissue may be placed at the outside of the flexible tube. The fixing element is an insulated wire 17 having a zig-zag shaped section 8 or a V-shaped section 9. Other fixing elements shaped differently such as e.g. notes, loops, hooks and the like may also be used.

Figure 3:
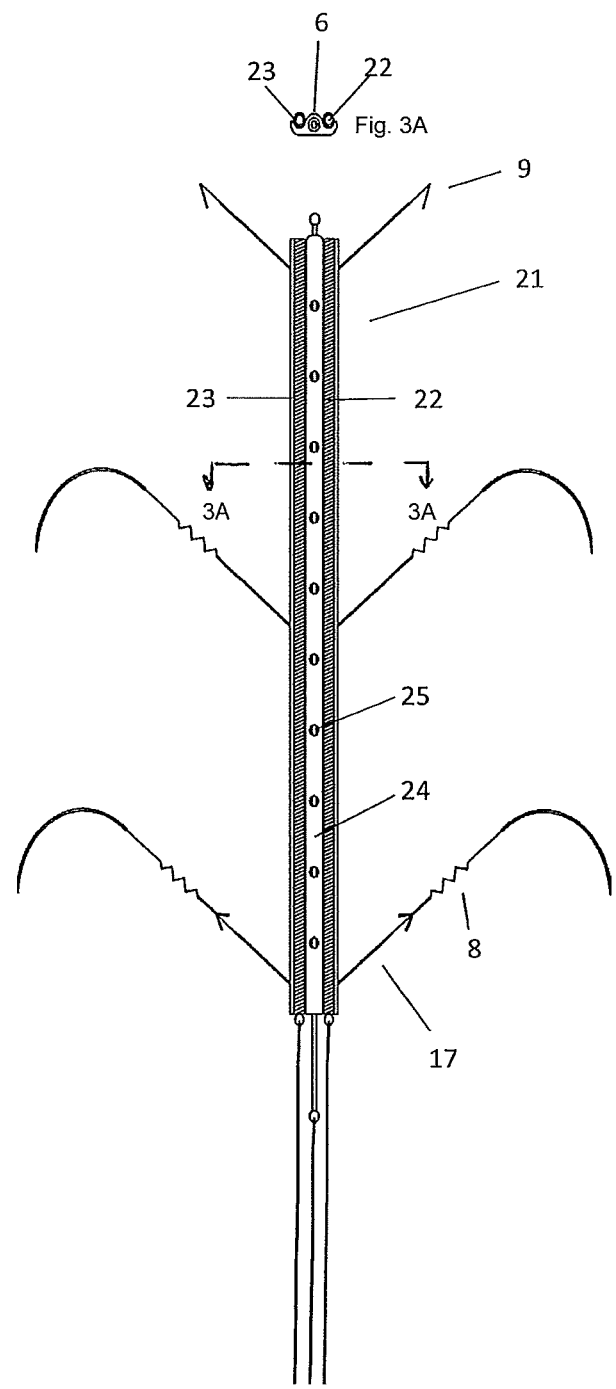
FIG. 3 shows an alternate embodiment of the epicardial mapping electrode, the electrode lead with the associated pole being centrally placed.

FIG. 3 shows an exemplary mapping electrode 21 comprising a flexible tube 24 having a proximal and a distal end, and having a lumen 6 extending from the proximal to the distal end for inserting an insulated movable electrode lead with its associated electrical pole 6, said flexible tube being centrally arranged. The mapping electrode comprises two coil shaped indifferent electrodes 22 and 23 being placed directly adjacent and parallel to the flexible tube and extending from the proximal to the distal end. The flexible tube has along the electrode lead a number of openings 25 facing the surface of the heart said openings providing contact between the myocardial tissue and the electrical pole. The openings 25 are aligned in a vertical line which is coaxial to the longitudinal axis of the tube 24.

Figure 4:
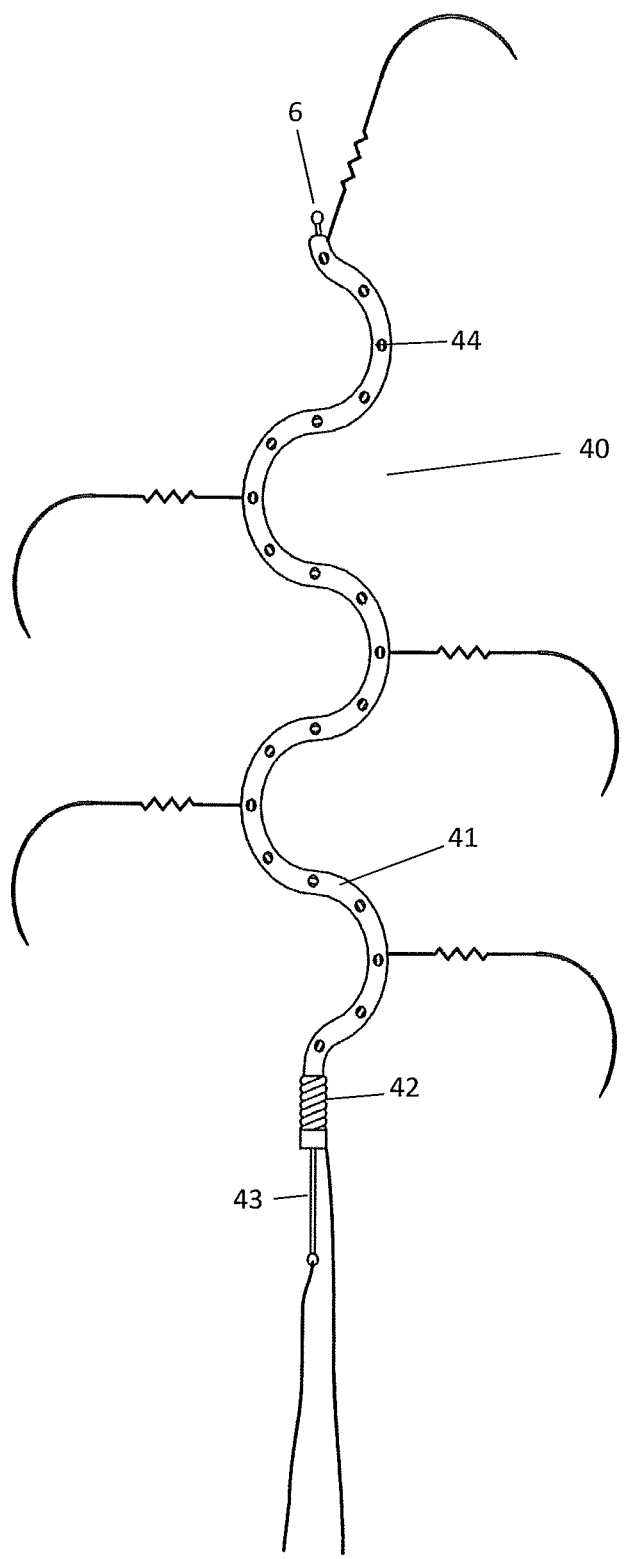
FIG. 4 shows an alternate embodiment of the epicardial mapping electrode in a curved shape.

FIG. 4 shows an exemplary mapping electrode 40. The flexible tube 41 having a proximal and a distal end is formed in curved shape. The flexible tube has a lumen and a movable insulated electrode lead 43 arranged inside said lumen extending from the proximal to the distal end, the electrode lead having at its distal end an electrical pole 6 and at its proximal end a coil 42 forming the indifferent electrode. The openings 44 are arranged in curved shape along the electrode lead. The openings 44 are in line which is coaxial to the curved longitudinal axis of the tube 41.

By pulling the electrode lead 43 the electrical pole is moved towards an opening thus providing contact between the myocardial tissue and the electrode pole.

There are several advantages provided by the present invention. The inventive epicardial mapping electrode allows an optimum monitoring of cardiac activity after cardiac surgery. Due to the fact that the electrode poles are movable and adjustable towards each other and are associated with the line of openings systematic mapping of the heart section is possible, thus defining the optimum section of the left ventricle for configuring and situating a permanent pacing electrode. The resynchronization therapy can thus be improved. If required a number of inventive mapping electrodes can be used in parallel thus allowing to map a huge section of the heart. The inventive mapping electrode is easily removable after use through an opening made in the chest wall, comparable to the pulling back of heart wires.

The methods and systems of the present invention, as described above and shown in the drawings, provide for an epcardial mapping electrode. While the apparatus and methods of the subject invention have been shown and described with reference to preferred embodiments, those skilled in the art will readily appreciate that changes and/or modifications may be made thereto without departing from the spirit and scope of the subject invention.

What is claimed is:

1. An epicardial mapping electrode suitable for temporarily mapping and/or stimulating the left ventricle after a cardiac surgery comprising:
   a flexible tube having a proximal and a distal end and a longitudinal structure therebetween, the tube has at least one lumen; and
   a movable insulated electrode lead arranged inside the lumen, the electrode lead being a partly insulated coil, the lumen together with the electrode lead extends longitudinally through said longitudinal structure, the electrode lead has at its distal end an electrical pole,
   wherein the flexible tube includes a plurality of openings along the longitudinal structure between the proximal and distal ends of the tube, said openings adapted to face the surface of the heart, said openings providing contact between the myocardial tissue and the electrical pole.

2. The epicardial mapping electrode according to claim 1 wherein the flexible tube is made of flexible material selected from the group consisting of silicone, polyurethane, polyester, silk and polyimide.

3. The epicardial mapping electrode according to claim 1 wherein the flexible tube has two lumens for inserting two electrode-leads which are adjustable towards each other.

4. The epicardial mapping electrode according to claim 1 wherein a stylet is located inside the electrode lead.

5. The epicardial mapping electrode according to claim 1 wherein the flexible tube includes a nitinol thread to support the design.

6. The epicardial mapping electrode according to claim 1 wherein fixing elements are included at the outside of the flexible tube.

7. The epicardial mapping electrode according to claim 1 further comprising an indifferent counter-electrode, wherein the indifferent counter-electrode is a coil of the electrode lead extending longitudinally through the flexible tube.

8. The epicardial mapping electrode according to claim 7 wherein two indifferent electrodes are located directly adjacent and parallel to the flexible tube containing the insulated electrode lead with the electrical pole at its distal end.

9. The epicardial mapping electrode according to claim 7 wherein the indifferent counter-electrode is separately located at the proximal end of the flexible tube.

\* \* \* \* \*